(12) United States Patent
Van 'T Hof et al.

(10) Patent No.: US 11,266,532 B2
(45) Date of Patent: Mar. 8, 2022

(54) ACOUSTIC FILTER WITH ATTENUATION CONTROL

(71) Applicant: DYNAMIC EAR COMPANY B.V., Delft (NL)

(72) Inventors: Pieter Gerard Van 'T Hof, Delft (NL); Adrián Lara-Quintanilla, Delft (NL); Engbert Wilmink, Delft (NL)

(73) Assignee: SONOVA AG, Staefa (CH)

( * ) Notice: Subject to any disclaimer, the term of this patent is extended or adjusted under 35 U.S.C. 154(b) by 37 days.

(21) Appl. No.: 16/963,758

(22) PCT Filed: Jan. 25, 2019

(86) PCT No.: PCT/NL2019/050043
§ 371 (c)(1),
(2) Date: Jul. 21, 2020

(87) PCT Pub. No.: WO2019/147131
PCT Pub. Date: Aug. 1, 2019

(65) Prior Publication Data
US 2020/0352788 A1    Nov. 12, 2020

(30) Foreign Application Priority Data
Jan. 26, 2018    (NL) ..................................... 2020330

(51) Int. Cl.
*H04R 25/00*    (2006.01)
*A61F 11/08*    (2006.01)
*H04R 1/10*    (2006.01)

(52) U.S. Cl.
CPC ............ *A61F 11/08* (2013.01); *H04R 1/1016* (2013.01); *H04R 1/1041* (2013.01);
(Continued)

(58) Field of Classification Search
CPC .... H04R 1/1016; H04R 1/105; H04R 1/1086; H04R 1/1075; H04R 1/1058;
(Continued)

(56) References Cited

U.S. PATENT DOCUMENTS 9,516,426 B2 * 12/2016 Pinkerton ................ H04R 7/02
10,805,746 B2 * 10/2020 Bolsman ................. H04R 25/65
(Continued)

FOREIGN PATENT DOCUMENTS

EP          2124477 A2    11/2009
WO      2005/041831 A1     5/2005
(Continued)

OTHER PUBLICATIONS

International Search Report dated Jul. 9, 2019 issued in corresponding International Application No. PCT/NL2019/050043 (3 pgs.).
(Continued)

*Primary Examiner* — Amir H Etesam
(74) *Attorney, Agent, or Firm* — Pillsbury Winthrop Shaw Pittman, LLP (57) ABSTRACT

An acoustic filter including a valve system with acoustic valves arranged in a sound passage for controlling the acoustic resistance of respective apertures based on a control signal for selecting an attenuation of a sound pressure level of transmitted sound compared to that of received sound. The acoustic filter is adapted to provide the selection of the attenuation from a sequence of predetermined attenuations based on a selection of the control signal. Each attenuation in the sequence corresponds to acoustic valves providing the apertures with a respective predetermined acoustic resistance, wherein the acoustic resistances of subsequent attenuations in the sequence are adapted to correspond with a linear increase or decrease in the attenuation of the sound in decibels.

16 Claims, 7 Drawing Sheets

(52) U.S. Cl.
CPC ......... *H04R 25/652* (2013.01); *H04R 25/658* (2013.01); *A61F 2011/085* (2013.01); *A61F 2240/001* (2013.01); *H04R 2225/025* (2013.01); *H04R 2225/61* (2013.01); *H04R 2460/11* (2013.01)

(58) Field of Classification Search
CPC ................ H04R 1/1066; H04R 25/652; H04R 2225/025; H04R 5/0335; H04R 1/10; H04R 1/2786; H04R 1/1083
See application file for complete search history.

(56) References Cited

U.S. PATENT DOCUMENTS

| | | | |
|---|---|---|---|
| 2006/0045299 | A1 | 3/2006 | Haussmann |
| 2012/0318605 | A1 | 12/2012 | Brown |
| 2014/0270257 | A1 | 9/2014 | Bauman et al. |
| 2016/0212529 | A1 | 7/2016 | Epping |
| 2016/0255433 | A1 | 9/2016 | Grinker |

FOREIGN PATENT DOCUMENTS

| | | |
|---|---|---|
| WO | 2007/097627 A1 | 8/2007 |
| WO | 2014/030998 A1 | 2/2014 |
| WO | 2017/203218 A1 | 11/2017 |

OTHER PUBLICATIONS

International Preliminary Report on Patentability dated Jul. 28, 2020 issued in corresponding International Patent Application No. PCT/NL2019/050043 (7 pgs ).

Written Opinion of the International Searching Authority dated Jul. 9, 2019 issued in corresponding International Patent Application No. PCT/NL2019/050043 (6 pgs.).

Pauline Poncet et al., "Static and Dynamic Studies of Electro-Active Polymer Actuators and Integration in a Demonstrator", Actuators 2017, 6, 18; doi:10.3390/act6020018, pp. 1-10.

* cited by examiner

ACOUSTIC FILTER WITH ATTENUATION CONTROL

CROSS-REFERENCE TO RELATED APPLICATIONS

This application is the U.S. National Stage of PCT/NL2019/050043, filed Jan. 25, 2019, which claims priority to: Netherlands Patent Application No. 2020330, filed Jan. 26, 2018, the entire contents of both of which are herein incorporated by reference in their entireties.

TECHNICAL FIELD AND BACKGROUND

The present disclosure relates to an acoustic filter for attenuating sound in an earplug, a method for manufacturing the acoustic filter, and use of the acoustic filter.

Various products like hearables, hearing aids, earphones, and headphones can provide an acoustical seal to the ear. Wearing such product may give the user a feeling of being occluded and cut off from their surroundings. Furthermore, prolonged use may lead to irritated ears, as the ears are not ventilated. Hence some of these products may include an ambient channel or sound passage to provide an open (acoustical) pathway through the otherwise sealed housing. Typically, such channel provides two modes. In an open mode it preserves natural hearing, and in a closed mode the environment is blocked to protect the ear from undesired ambient sound and/or to provide enhanced sound quality (compared to open mode sound) when an acoustic generator is present.

For example, WO 2005/041831 A1 describes an earplug comprising a plug member for blocking a person's ear canal, said plug member comprising at least one acoustic channel for channeling incoming acoustic energy into said person's ear, said earplug further comprising a detector for detecting an acoustic energy level or for detecting a control signal that is indicative for an acoustic energy level to be received, an acoustic valve positioned in said channel, and a control unit that, in response to said detector, controls said valve so as to attenuate the acoustic energy channeled through said acoustic channel.

There remains a desire to improve control over attenuation of sound using acoustic valves.

SUMMARY

Aspects of the present disclosure relate to an acoustic filter and earplug comprising the filter. In preferred embodiments, the acoustic filter comprises a filter housing. Typically, the acoustic filter or housing is placeable or integrated in an earplug. In this way a seal is formed between an auditory canal of an ear and an external surroundings. A sound passage may extend through the filter for receiving sound from the external surroundings and transmitting the sound into the auditory canal. The sound passage can have one or more apertures. The passage and apertures can provide an acoustic resistance for the sound received and transmitted there through. In preferred embodiments, the filter comprises a valve system with one or more acoustic valves arranged in the sound passage. The valves may control the acoustic resistance of the one or more apertures e.g. based on a control signal. In this way an attenuation of a sound pressure level of the transmitted sound can be selected.

Advantageously, the acoustic filter can be adapted to provide the selection from a sequence comprising a number of predetermined attenuations. For example the selection can be made from a discrete number of programmed sound levels. The selection may typically involve sending the corresponding control signal which can also be preselected, e.g. programmed into a controller or hardwired in circuitry. Each attenuation in the sequence may correspond to one or more acoustic valves providing one or more respective apertures with predetermined acoustic resistance. In some preferred embodiments, the acoustic resistances of subsequent attenuations in the sequence are adapted to correspond with a (near) linear increase or decrease in the attenuation of the sound as measured in decibels. This may correspond to logarithmic variation of the relative sound pressure level.

It is recognized that attenuating the sound pressure level on a logarithmic scale, may better conform to human hearing and thus improve desired control over the sound level. While conventional volume control may be realized by an electronic sound generator, the inventors find that improved control of ambient volume can be achieved using a preselected range of acoustic resistances which may not require electronic conversion of the sound. In some embodiments, the attenuation control may be improved by using multiple valves and/or adapted aperture shapes. For example, the tuning of acoustic resistances can be improved by combining predetermined aperture sizes that are selectively opened or closed. Additionally, or alternatively, partially opened valves can be used to provide intermediate acoustic properties. By shaping the aperture and/or valve, the open area can be more accurately determined.

Some aspects of the present disclosure may relate to methods of manufacturing acoustic filters, e.g. as described herein. For example, an acoustic filter can be specifically designed to provide a discrete number of attenuations which linearly increase or decrease the transmitted sound in decibels. For example, the corresponding sequence of control signals for control of the acoustic filter may be stored in software or hardware implementations. Some aspects of the present disclosure may also relate to the use of an acoustic filter, e.g. for controlling attenuation of the external surroundings into the auditory canal. For example, the use may comprise changing the attenuation in discrete steps, wherein in each step a subsequent attenuation in the sequence of predetermined attenuations is selected to linear increase or decrease in the attenuation of the sound in decibels.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

It is recognized that human senses such as hearing typically work in accordance with Weber-Fetcher law, i.e. wherein a perceived change such as volume or loudness of sound is logarithmically related to an actual change of the corresponding physical stimulus such as the sound pressure level or intensity entering the ear canal. So it may better conform to human experience to use a logarithmic scale for expressing attenuation of sound. For example, the decibel dB or dB SPL (sound pressure level) in acoustics can be used to quantify sound pressure levels and intensities relative to a reference on a logarithmic scale. For example, an intensity level "IL" of a sound intensity "I" can be expressed as $$IL = 10 \log_{10}\left(\frac{I}{I_{ref}}\right)[dB] \qquad (1)$$

where "$I_{ref}$" is a reference intensity. Alternatively or additionally, since the intensity carried by a traveling wave is typically proportional to the square of the pressure amplitude, the intensity level can be expressed by the sound pressure level (SPL) as $$SPL = 10 \log_{10}\left(\frac{P_e^2}{P_{ref}^2}\right) = 20 \log_{10}\left(\frac{P_e}{P_{ref}}\right)[dB] \qquad (2)$$

where "$P_e$" is the measured effective pressure amplitude of the sound wave and "$P_{ref}$" is the reference effective pressure amplitude. For example, the effective sound pressure is the root mean square of the instantaneous sound pressure over a given interval of time. For example for air, the pressure reference is usually taken to be $$P_{ref} = 20 \cdot 10^{-6} \ [Pa] \qquad (3)$$

the lowest sound pressure a human can hear, also called the threshold of hearing.

As described herein, sound attenuation "$\Delta S$" through a filter is expressed in decibel e.g. based on sound pressure levels of the sound "$S_0$" entering the filter and the sound "$S_N$" exiting the filter:

$$\Delta S = -20 \cdot \log_{10}\left(\frac{S_N}{S_0}\right)[dB] \qquad (4)$$

The factor 20 and base 10 of the logarithm are typically used in audiology for the expression in decibel. However, it will be recognized that the formula can be linearly scaled to other pre-factors and/or other based logarithms e.g. using mathematical conversion such as:

$$\log_b(x) = \frac{\log_d(x)}{\log_d(b)} \qquad (5)$$

Accordingly, the statement that the attenuation changes linearly (or in constant steps) on a decibel scale may be equivalent to any exponential changes or steps of the relative sound pressure level or intensity. Generally, the difference between linear and exponential steps may best be recognized when a sequence of at least three, preferably more different values are compared.

As described herein, attenuation of sound waves through an acoustic filter can be realized by blocking part of a canal and only allowing sound to enter through one or more apertures having relatively restricted dimensions e.g. compared to the rest of the filter. Without being bound by theory, it is found that the acoustic properties of filters can be described by parameters such as the acoustic resistance which may be a measure of the energy dissipation or non-transmittance of sound through the filter. For example, acoustic resistance can be defined as the real component of acoustic impedance e.g. expressed in acoustic ohms [Ω]. This quantity may be analogous in some ways to the quantity of electric resistance.

Without being bound by theory, it is found that the relative attenuation "$\Delta S$" of sound waves (in decibel) through an acoustic filter may be correlated with the relative acoustic resistance "$R_N$" of the filter or restricted sound passage according to a proportionality relation such as:

$$\Delta S_N \propto \log(R_N)[dB] \qquad (6)$$

Generally, it will thus be appreciated that an exponential increase of the acoustic resistance "$R_N$" may lead to a corresponding decrease in the sound pressure level of the transmitted sound "$S_N$" compared to the received sound "$S_0$" and/or a linear increase of the attenuation "$\Delta S$" as expressed in decibel.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1A:
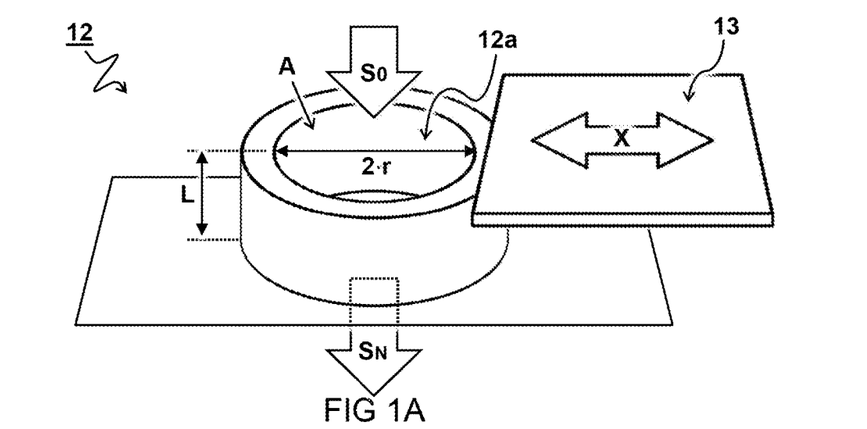
FIGS. 1A-1C schematically illustrate various dimensions of example apertures.

FIG. 1A illustrates an example, wherein acoustic resistance is provided by a circular duct forming an aperture 12a. Without being bound by theory, it is found that the resistance of such restricted passage may be modelled or approximated at least in relative terms using formulas such as:

$$R_{duct} = \frac{8\eta L}{\pi r^4} \propto \frac{L}{A^2} \quad (7)$$

where "η" is the viscosity of air (typically about 18.4 μPa·s), "L" is the depth or length of the duct, "r" is the radius of the duct, and "A" is the corresponding cross-section area of the duct (transverse to the main sound direction). It will be noted that the acoustic resistance of the aperture may increase very rapidly (with the fourth power of 1/r) as the radius of the duct or aperture decreases. A typical aperture for acoustic attenuation in an earplug may e.g. have a depth between 10-1000 μm, preferably between 50-500 μm, more preferably between 100-200 μm. The aperture may e.g. have a diameter between 10-2000 μm, preferably between 20-1000 μm, between 50-500 μm, or between 100-300 μm.

Without being bound by theory it may be observed that a circular aperture wherein half of the circle is closed off, e.g. by a valve 13 sliding along the direction "X" as shown, may not be have the same acoustic resistance as another circular aperture with half the cross-section area A (or the radius divided by square root of two). This can be explained e.g. by the predominant effect which may be played by the smallest restricting dimension of the aperture on the acoustic resistance. So the half closed aperture may exhibit an acoustic resistance which is more similar to a pair of parallel circular apertures each with half the radius $r_h = r_o/2$, and the relative increase in resistance can in some case be modelled or approximated at least in relative terms by:

$$\frac{R_{half\ duct}}{R_{open\ duct}} \approx \frac{1}{2} \cdot \frac{\frac{1}{r_h^4}}{\frac{1}{r_o^4}} = \frac{1}{2} \cdot \frac{\left(\frac{1}{2}r_o\right)^4}{\frac{1}{r_o^4}} = 8 \quad (8)$$

Thus closing half the duct from one side may increase the acoustic resistance as much as a factor eight instead of a factor four which would be the case if only the area should play a role. And the effect of restricting the passage can be even higher as the aperture is being further closed wherein the resulting attenuation may increase exponentially. This behavior is one reason which can make it relatively difficult to accurately control the acoustic resistance for setting a desired attenuation by means of a valve partially covering an aperture.

Figure 1B:
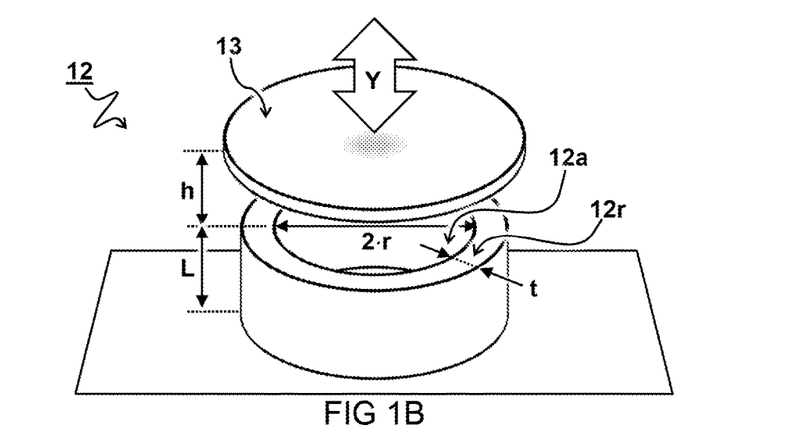

FIG. 1B illustrates an example wherein a valve 13 is added hovering at some distance above the exit of the duct or aperture 12a. It is found that the close presence of a valve may cause an additional acoustic resistance, e.g. due to a restriction formed by the slit between the valve 13 and the rim 12r forming the aperture 12a. For example, the additional acoustic resistance may be modelled or approximated at least in relative terms using formulas such as:

$$R_{valve} = \frac{12\eta t}{2\pi r \cdot h^3} \propto \frac{t}{b \cdot h^3} \quad (9)$$

where "η" and "r" have the same meaning as before, "t" is a thickness of the rim 12r, "h" is a distance or height between the valve and an exit of the duct (rim 12r), as shown, and "b" is a circumference length of the rim (not shown in the figure).

When acoustic resistances are encountered in series, e.g. as in the resistance of the duct and valve as shown, the total resistance "$R_{total}$" may be modelled or approximated at least in relative terms by addition, e.g. using:

$$R_{total} = R_{duct} + R_{valve} \quad (10)$$

It will be noted that the resistance of the valve slit may quickly vanish for larger distances "h" and the total resistance approaches the value of "$R_{duct}$", which is logical. On the other hand, the acoustic resistance can increase very rapidly (this time with the third power of 1/h) as the valve 13 closes the aperture 12a by decreasing the distance "h". Again, this can make it relatively difficult to accurately control the acoustic resistance for setting a desired attenuation.

Figure 1C:
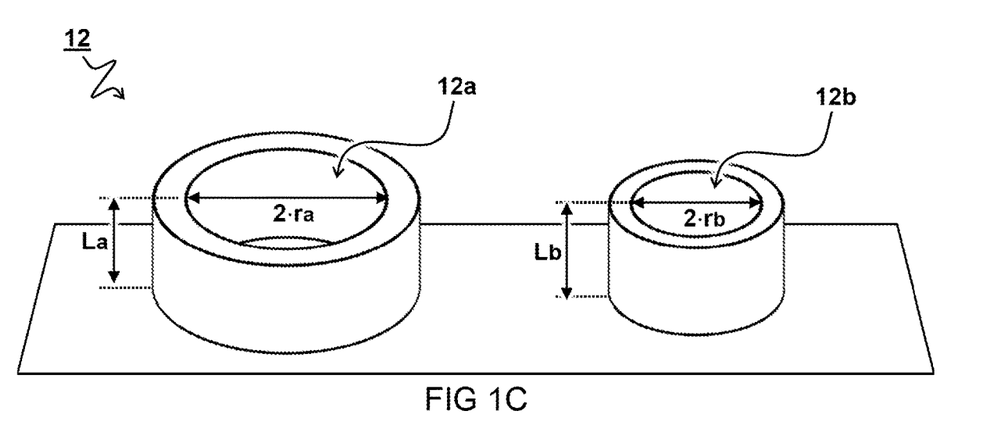

FIG. 1C illustrates yet another or further example wherein, the sound passage 12 comprises a plurality of apertures 12a, 12b through which the sound may travel. Each aperture may provide a respective acoustic resistance, which may be individually calculated e.g. using the formula for "$R_{duct}$" above. When multiple apertures are arranged as parallel channels for the sound to travel through, their combined total resistance may be modelled or approximated at least in relative terms using formulas such as:

$$1/R_{total} = 1/R_a + 1/R_b \quad (11)$$

where "$R_a$" and "$R_b$" are the respective acoustic resistances of the individual apertures. It will thus be appreciated that a combination of multiple apertures each having a different radius or cross-section (or different depth "L") may be used to control a desired acoustic resistance in a more reproducible way than by e.g. half closing a valve. For example, a total resistance of two open apertures with the same depth "L" and different radii "$r_a$" and "$r_b$", as shown, can be modelled using:

$$R_{total} = \left(\frac{8\eta L}{\pi}\right) \cdot \frac{1}{(r_a^4 + r_b^4)} \quad (12)$$

Additional resistances can be determined by simply closing the respective apertures 12a, 12b completely. For example in this way the following sequence of relative acoustic resistances (from small to big) can be realized:

$$\left(\frac{8\eta L}{\pi}\right) \cdot \left[\frac{1}{(r_a^4 + r_b^4)}; \frac{1}{(r_a^4)}; \frac{1}{r_b^4}\right] \quad (13)$$

Figure 2A:
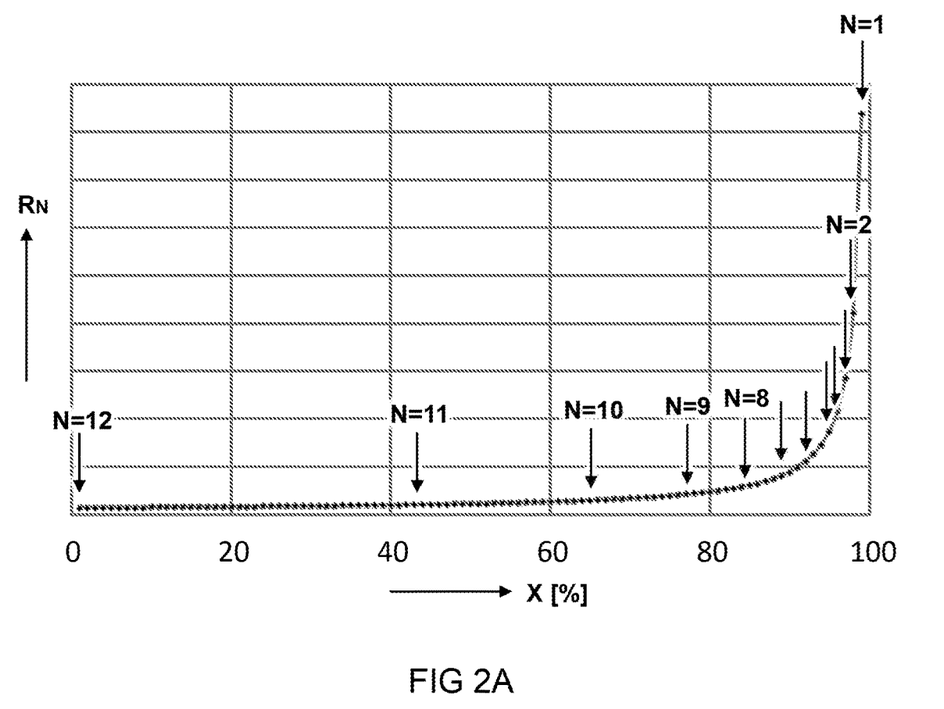
FIG. 2A schematically illustrates a general trend of acoustic resistance as a function of one or more apertures being closed.

FIG. 2A schematically illustrates a general trend of acoustic resistance "$R_N$" as a function of one or more apertures being closed between zero percent (fully open) and hundred percent (fully closed). In this case the graph is calculated by taking the combined acoustic resistance of a hundred parallel apertures with the same dimensions and closing them one by one. It will be noted that the acoustic resistance increases dramatically, especially when the one or more apertures are almost completely closed.

Figure 2B:
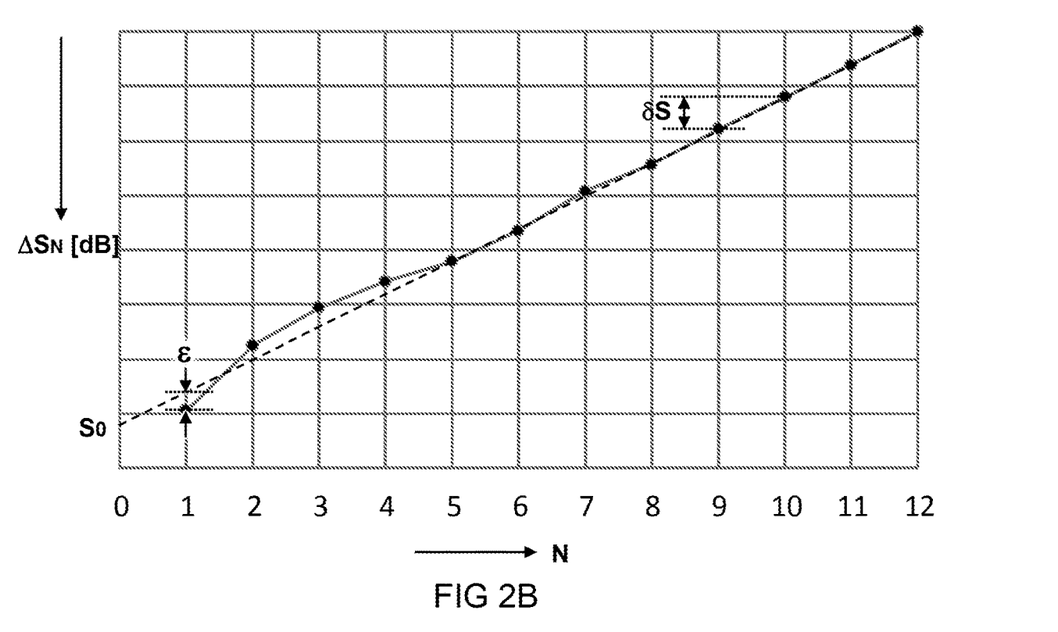
FIG. 2B schematically illustrates a selection of attenuations.

FIG. 2B schematically illustrates a relative attenuation $\Delta S_N$ (in decibel) corresponding to a logarithm of the acoustic resistances $R_N$ at a sequence of discrete steps N selected from values in the graph of FIG. 2A as indicated. In this case, the acoustic values for the acoustic resistances $R_N$ are selected such that the relative attenuation $\Delta S_N$ in decibel has a near linear increase with each subsequent step.

For example, a selected sequence of relative attenuations $\Delta S_N$ in decibel may be described by the clashed trend-line in as shown in the graph, e.g. obtained by least squares fitting the points. Preferably, the relative attenuations in the sequence can be described at least qualitatively e.g. using a formula such as $$\Delta S_N = S_0 + \delta S \cdot N^x \pm \epsilon \, [dB] \quad (14)$$

wherein "$S_0$" is an attenuation offset e.g. minimum or maximum attenuation for extrapolated step 0, "N" is the step number in the sequence e.g. an integer number, "$\delta S$" is a step size indicating the relative increase of the attenuation for each step, and "x" is an exponent which is preferably as close as possible to 1 for the desired linear behavior (in decibel), e.g. $0.8 \leq x \leq 1.2$, preferably $0.9 \leq x \leq 1.1$, more preferably $0.95 \leq x \leq 1.05$, most preferably $0.99 \leq x \leq 1.01$.

It will be noted that the linear approximation may be more difficult for larger attenuations, i.e. less open area, e.g. at N=1 to N=4. For these or other reasons, points may deviate from the trend-line, e.g. within an acceptable error margin "$\epsilon$". For example, the error margin "$\epsilon$" may be defined relative to the step size $\delta S$, e.g. $\epsilon \leq 0.5 \cdot \delta S$, preferably $\epsilon \leq 0.1 \cdot \delta S$, more preferably $\epsilon \leq 0.05 \cdot \delta S$, most preferably $\epsilon \leq 0.1 \cdot \delta S$, or smaller. Alternatively, or in addition, the error margin "$\epsilon$" may be defined simply in decibel, e.g. less than one decibel, preferably less than half a decibel, more preferably less than a tenth of a decibel, or less, e.g. $0.0001 \, dB \leq \epsilon \leq 1 \, dB$. In some cases it may also be acceptable that not all possible selections for the attenuation are at or near the line. For example, there may be one or more outliers, e.g. when using a relatively large aperture and valve for completely opening the acoustic filter in a setting with minimal attenuation. Alternatively, or in addition, when all valves are closed, the attenuation may be arbitrarily high and limited by other factors such as the seal of the earplug.

Figure 3A:
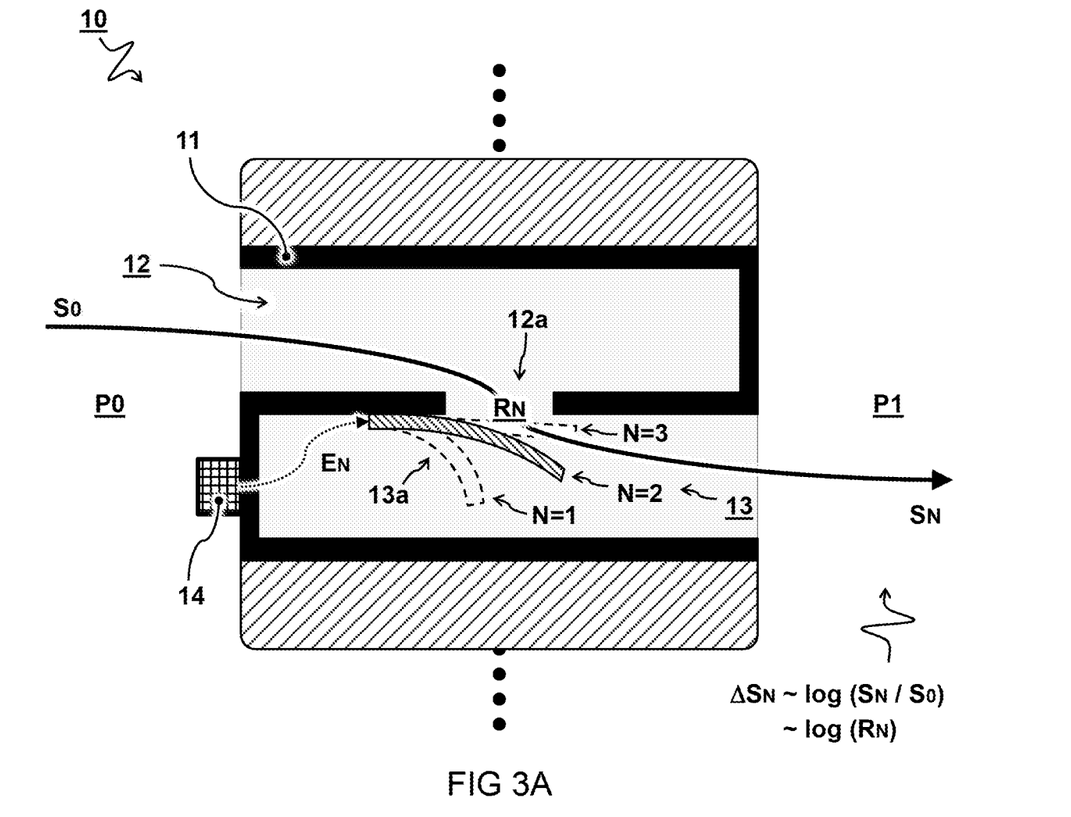
FIG. 3A illustrates an embodiment of an acoustic filter.
Figure 3B:
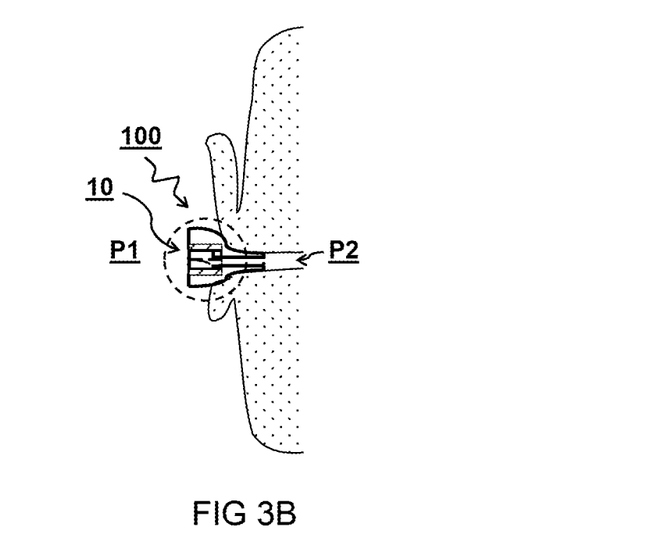
FIG. 3B illustrates an embodiment of an earplug.

FIG. 3A illustrates an embodiment of an acoustic filter 10. FIG. 3B illustrates an embodiment of the acoustic filter 10 in an earplug 100. For example, a customized ear mould or universal earplug may be used.

In the embodiment shown, the acoustic filter 10 comprises a filter housing 11 which may be placeable or integrated in the earplug 100. The housing or earplug may form a seal between an auditory canal $P_1$ of an ear and an external surroundings $P_0$. A sound passage 12 may extend through the filter housing 11 for receiving sound $S_0$ from the external surroundings $P_1$ and transmitting the sound $S_1$ into the auditory canal $P_1$. The sound passage 12 may have, e.g. form or define, one or more apertures 12a (one shown here). The apertures may determine in large part an acoustic resistance $R_N$ for the sound received and transmitted through the sound passage 12.

In the embodiment shown, the filter comprises a valve system 13. The valve system 13 may comprise one or more acoustic valves 13a (one shown here). The valves can be arranged in the sound passage 12 for controlling the acoustic resistance $R_N$ of the one or more apertures 12a. For example, the valves are controlled based on an electrical or other control signal $E_N$.

In some embodiments, the acoustic filter 10 is adapted to provide the selection of the attenuation $\Delta S_N$. For example, the attenuation is selected from a sequence comprising a discrete number "N" of predetermined attenuations. Preferably, at least three predetermined attenuations are provided, preferably more, e.g. at least four, at least five, at least ten, e.g. between twenty and hundred, or more. Instead of a discrete number it may also be envisaged to provide as many different settings as possible, e.g. depending on digital circuitry.

In some embodiments, the selection of the attenuation may comprise selection of a control signal $E_N$ to the valve system. For example, a control signal is selected from a corresponding sequence of predetermined control signals $E_1, E_2, E_3$. Each attenuation $\Delta S_N$ in the sequence may correspond to one or more acoustic valves 13a providing one or more apertures 12a with a respective predetermined acoustic resistance $R_N$. Typically, the selection of an attenuation may take place via a volume control, e.g. integrated in a controller or coupled there with. Also other types of control are possible, e.g. based on measurements. In some preferred embodiments, the acoustic resistances of subsequent attenuations in the sequence are adapted to correspond with a linear increase or decrease in the attenuation $\Delta S_N$ of the sound in decibels. Preferably, the attenuation is relatively constant over different frequencies at least in an audible frequency range. Alternatively, or in addition, the attenuation may be defined at a specific one or more frequencies of the sound, e.g. at 200 Hz or any other audible frequency.

In one embodiment, the valve system 13 is configured to control a total opening cross-section "A" through the sound passage 12 by actuating the one or more acoustic valves 13a relative to the one or more apertures 12a. For example, each acoustic valve 13a comprises a respective flap or other passage restricting element configured to at least partially close or open the respective aperture 12a by sliding, pivoting, lifting, bending, or other relative movement of the restricting element relative to the aperture. In some embodiments, the acoustic valves 13a comprise an actuator, e.g. electromechanical transducer or material which may provide electrically controllable movement of the valve, e.g. flap. Preferably, the acoustic valves 13a comprise a piezoelectric material for actuating the valves. For example, the acoustic valves 13a comprise ceramic piezoelectric benders which may form both actuator and flap. Alternatively, or additionally the acoustic valves 13a may comprise active polymer benders which can have the further advantage of providing a smaller bending radius B, in some embodiments. Advantageously, these or other acoustic valves may be constructed in a MEMS process out of one plate of piezoelectric material, in some embodiments.

In some embodiments, the system comprises or communicates with a controller 14 which may be integrated with the filter housing or earplug, or provided in a separate dedicated or general control unit. In one embodiment, the controller is configured and/or programmed to provide the selection of the control signal $E_N$ for linearly varying the attenuation $\Delta S_N$ in decibels. For example, the controller 14 provides a predetermined sequence of volume settings wherein an increase or decrease of the volume results in a fixed change of the attenuation $\Delta S_N$ in decibels and/or logarithmic change of the sound pressure level. The volume settings may e.g. be stored in a table linked with corresponding control signals, and/or hardwired into circuitry.

In some embodiments, a controller can thus be used for selecting an attenuation $\Delta S_N$ of a sound pressure level of the transmitted sound $S_1$ compared to that of the received sound $S_0$. Manual control over the sound level preferably lets the acoustic filter react linearly in decibel (i.e. logarithmically in SPL) to user input, e.g. via volume knob or volume input from another device, e.g. smartphone. In other or further embodiments (not shown), the acoustic filter 10 comprises a microphone or pressure sensor for measuring the internal sound pressure level in the auditory canal. In some cases, the control signal $E_N$ can based, at least in part, on an output of the microphone. For example, alternatively, or in addition to controlling the attenuation manually, the controller may automatically increase attenuation in response to excessive ambient sound. There may also be an external microphone e.g. for measuring ambient sound such as human speech and automatically decrease the attenuation in response thereto. Also combinations of control are possible based on internal/external microphones anchor other sensors. The acoustic filter 10 may also provide further functionality, e.g. by integrating or cooperating with an acoustic generator. For example, the generator may be arranged between the valve and the auditory canal arranged for generating an acoustic signal into the auditory canal.

The acoustic filter 10 as described herein can be manufactured e.g. by designing the filter to provide a discrete number "N" of attenuations $\Delta S_1, \Delta S_2, \Delta S_3$ which linearly increase or decrease the transmitted sound in decibels. Some embodiments may comprise storing the corresponding sequence of control signals $E_1, E_2, E_3$ for control of the acoustic filter 10, e.g. in software or hardware. Also other methods of manufacturing may be envisaged.

The acoustic filter 10 as described herein can be used in various application, e.g. for controlling attenuation of the external surroundings $P_0$ into the auditory canal $P_1$. For example, such use may comprise changing the attenuation $\Delta S_N$ in discrete steps, wherein in each step a subsequent attenuation in the sequence of predetermined attenuations $\Delta S_1, \Delta S_2, \Delta S_3$ is selected to linear increase or decrease in the attenuation $\Delta S_N$ of the sound in decibels. Also other uses may be envisaged.

Figure 4A:
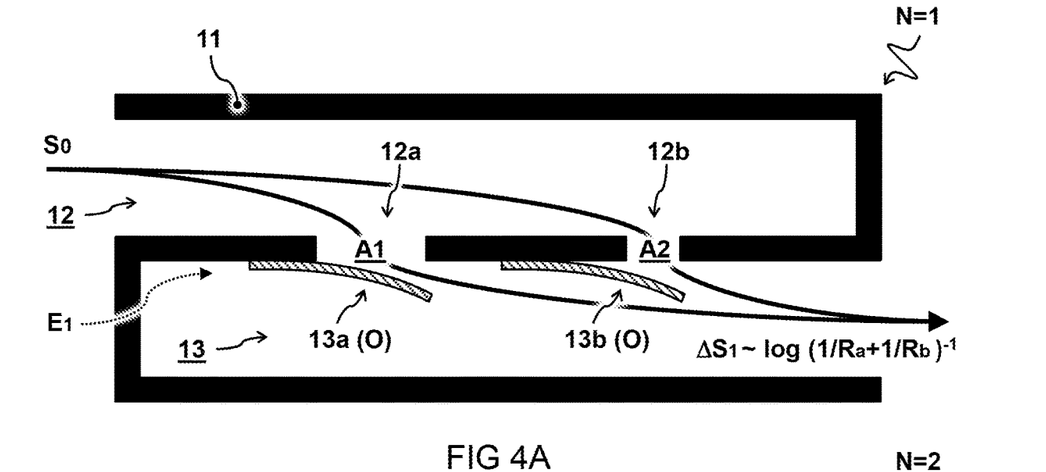
FIGS. 4A-4C illustrate an embodiment of a sound passage with multiple apertures.
Figure 4B:
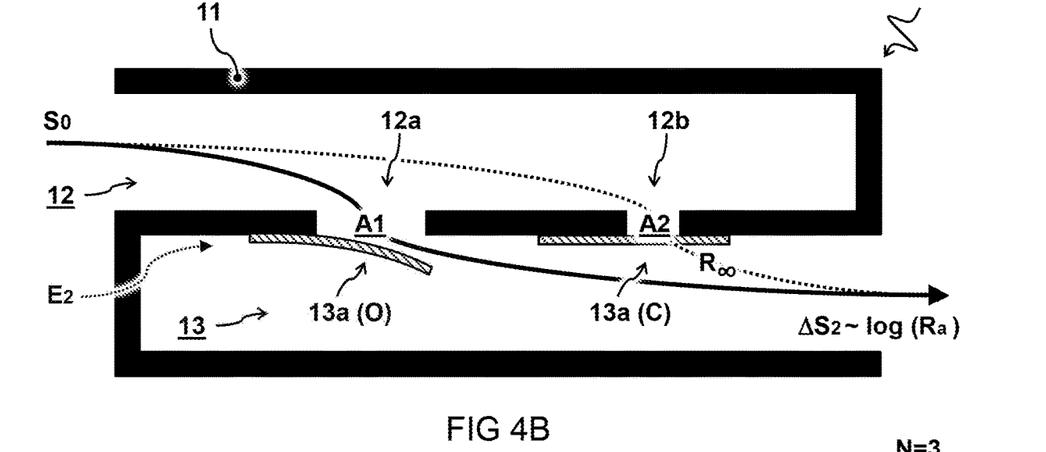
Figure 4C:
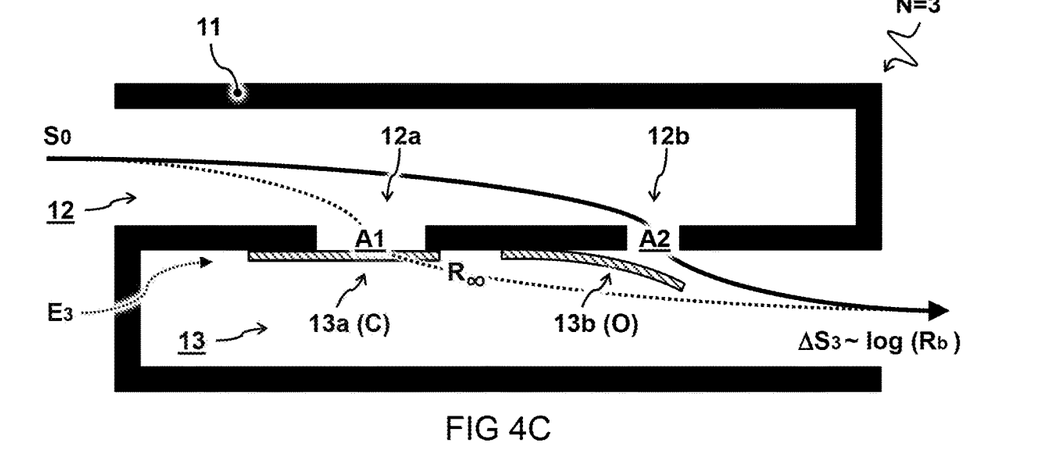
Figure 5A:
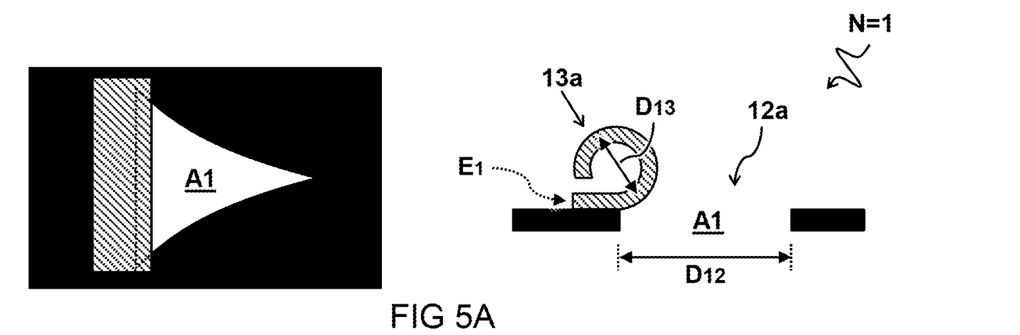
FIGS. 5A-5D schematically illustrate top and side views of an embodiment comprising a non-linear shaped aperture.
Figure 5B:
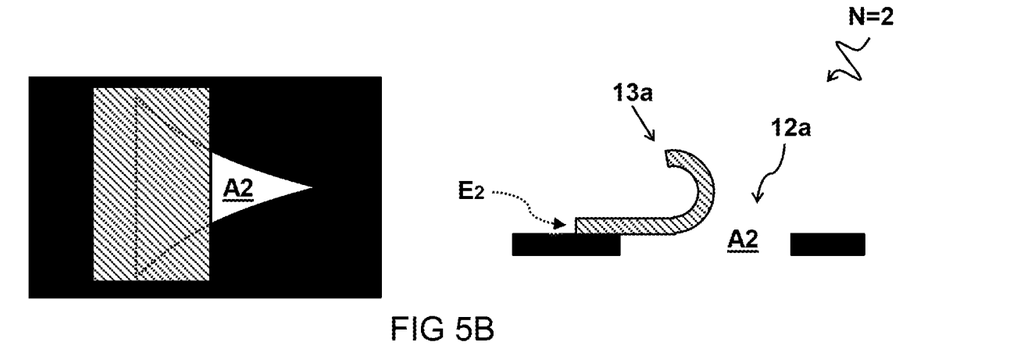
Figure 5C:
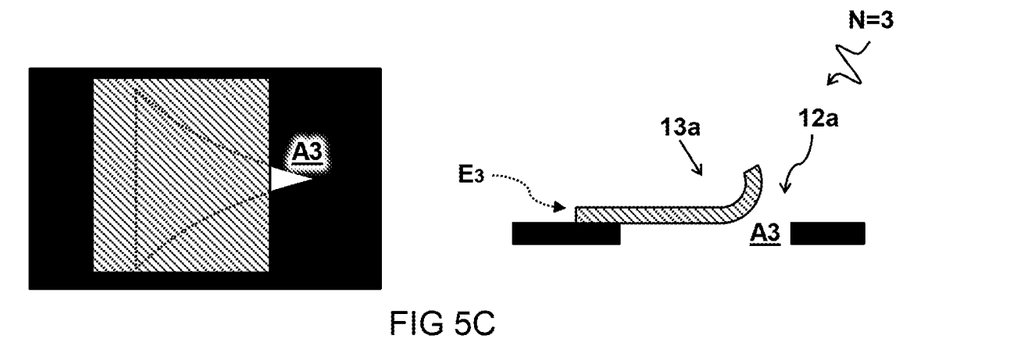
Figure 5D:
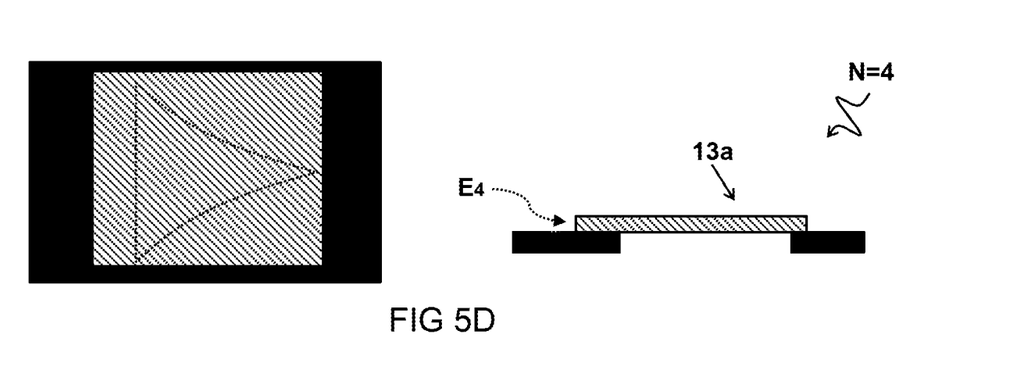

FIGS. 4A-4C illustrate an embodiment of a sound passage 12 with multiple apertures 12a,12b.

In one embodiment one or more acoustic valves are configured to open or close the respective one or more apertures. In the embodiment shown, the sound passage 12 comprises a plurality of apertures 12a,12b. In some preferred embodiments, at least some of the apertures 12a,12b individually have a different predetermined respective acoustic resistance Ra, Rb. For example, the different apertures have different opening cross-sections A1,A2 and/or different depths (not shown).

In some embodiments, e.g. as shown, the valve system 13 comprises a plurality of acoustic valves 13a,13b. Preferably, the valve system 13 is configured to provide the predetermined attenuations $\Delta S_1, \Delta S_2, \Delta S_3$ by combining respective acoustic resistances R of the plurality of apertures 12a,12b. For example, each acoustic valve 13a is configured to selectively switch between at least two predetermined sub-states "O" or "C" changing the respective apertures 12a to provide one of a predetermined selection of acoustic resistances Ra,R∞.

Preferably, the sub-states of a respective valve 13a include at least a fully open state "O", e.g. wherein the respective aperture is open with negligible or no restriction of the valve to provide a well-controlled predetermined acoustic resistance Ra depending predominantly on the dimensions of the aperture 12a. Preferably, the sub-states of a respective valve 13a include at least a fully closed state "C" wherein the respective aperture is closed off providing a very high acoustic resistance R∞ which may be virtually independent of the dimensions of the aperture 12a e.g. with negligible or no sound being transmitted there through. In some embodiments, one or more valves are adapted to optionally provide more than two sub-states, e.g. one or more intermediate state (not shown here) wherein the respective aperture is partially closed off between a fully open state "O" and a fully closed state "C" to provide an intermediate acoustic resistance. The intermediate acoustic resistance may e.g. be higher than the fully open state "O" and lower than the fully closed state "C". The intermediate resistance may be dependent on both the dimensions of the aperture 12a and a relative position and/or shape of the respective valve and therefore relatively difficult to control for some embodiments.

In some embodiments, combinations of sub-states "O" or "C" of multiple valves 13a,13b, controlling combinations of different individual acoustic resistances Ra,Rb are adapted to provide a number "N" of predetermined attenuations $\Delta S_1, \Delta S_2, \Delta S_3$ as describe herein. Preferably the states linearly increase or decrease the attenuation $\Delta S$ of the sound in decibels.

In some embodiments, the number "N" of predetermined attenuations provided by the combination of valves is greater than the number of valves itself. In other words, at least some attenuations are provided by different combinations of valves, e.g. at least two open valves. For example, in the embodiment shown combinations of sub-states "O" or "C" of two of the valves 13a,13b, controlling combinations of different individual acoustic resistances Ra,Rb, are configured to provide at least three of the predetermined attenuations $\Delta S_1, \Delta S_2, \Delta S_3$.

In the embodiment shown in FIG. 4A, a first attenuation $\Delta S_1$ may be provided by the valve system 13 opening two valves 12a,12b. This may provide a combined acoustic resistance which may be calculated with the law of parallel resistances using R1=1/(1/Ra+1/Rb). In the embodiment shown in FIG. 4B, a second attenuation $\Delta S_2$ may be provided by the valve system 13 closing the second valve 13b associated with the smaller aperture 12b while keeping the first valve 13a open. Because the acoustic resistance through the second valve is thus very high (R∞), the combined acoustic resistance may be very close to that of the larger aperture 12a alone, i.e. R2=Ra. In the embodiment shown in FIG. 4C, a third attenuation $\Delta S_3$ may be provided by the valve system 13 closing the first valve 13a associated with the bigger aperture 12a while keeping the second valve 13b open. Because the acoustic resistance through the first valve is thus very high R∞, the combined acoustic resistance may be very close to that of the smaller aperture 12b alone, i.e. R3=Rb. In this way the two different apertures may provide a series of at least three different acoustic resistances. For example, this may have the advantage of saving the limited space inside the earplug In some embodiments, it may be preferred to provide the same linear increase in decibel between the attenuations $\Delta S_1$ and $\Delta S_2$ as between the attenuations $\Delta S_2$ and $\Delta S_3$, wherein the following relations may hold:

$$\Delta S_2 - \Delta S_1 = \Delta S_3 - \Delta S_2 \tag{15}$$

$$\log(Ra) - \log\left(\frac{1}{Ra} + \frac{1}{Rb}\right)^{-1} = \log(Rb) - \log Ra \tag{16}$$

$$Ra \cdot \left(\frac{1}{Ra} + \frac{1}{Rb}\right) = \frac{Rb}{Ra} \tag{17}$$

$$\left(\frac{Ra + Rb}{Rb}\right) = \frac{Rb}{Ra} \tag{18}$$

Interestingly, this equation may be solved by choosing relative values for the acoustic resistances Ra and Rb in accordance with the golden ratio:

$$Rb = \frac{1+\sqrt{5}}{2} \cdot Ra \equiv \phi \cdot Ra \tag{19}$$

where φ≈1.618033 . . . . Of course also deviations from the golden ratio may be acceptable, e.g. φ±0.2, preferably φ±0.1, more preferably φ±0.05, most preferably as close to φ as possible or practical.

In some embodiments, at least some of the predetermined attenuations are provided by combinations of multiple open valves. For example, a combination of valves may be used to provide a combined acoustic resistance that is an interpolation or extrapolation of two or more acoustics resistances provided by individual valves or other combinations of valves on the linear decibel scale of the attenuation $\Delta S_N$. While the present embodiment shows only two valves, in other or further embodiments, the valve system 13 may comprise at least three valves for opening or closing respective apertures each having different acoustic resistances, preferably at least four, at least five, or more, e.g. between ten and forty valves, e.g. thirty-two valves.

FIGS. 5A-5D schematically illustrate top and side views of an embodiment comprising a valve in various states of opening.

In one embodiment, at least one of the acoustic valves 13a is configured to set a partially opened apertures 12a providing one or more of the predetermined acoustic resistances $R_N$. In another or further embodiment, a sequence of predetermined control signals $E_1, E_2, E_3$ causes, a total cross-section "A" of the at least one aperture 12a to sub-linearly decrease between a maximally opened state "O" and a maximally closed state "C". In other words, the cross-section changes more slowly when the acoustic valve is nearly closed than when it is nearly open. This may compensate, at least in part, for the fact that the acoustic resistance may rapidly increase when an aperture is almost closed. In other or further embodiments (not shown), the sequence of predetermined control signals $E_1, E_2, E_3$ causes, a height of at the least one acoustic valve 13a to sub-linearly lower between a maximally opened state "O" and a maximally closed state "C". In other words, the height of the valve above the aperture may change more slowly when the acoustic valve is nearly closed than when it is nearly open. Again, this may be related to the observation that the acoustic resistance may rapidly increase when the valve is almost closed.

In some embodiments, at least one aperture 12a and/or acoustic valve 13a is adapted to provide a non-linear change of its acoustic resistance $R_N$ in responds to a linear change of a voltage or current in the control signal $E_N$. For example, at least one aperture 12a and/or acoustic valve 13a is adapted to provide a logarithmically or exponentially changing open area for a linear motion of the acoustic valve 13a with respect to the aperture 12a.

In some embodiments, e.g. as shown, at least one aperture 12a has a tapered shape. This means a cross-section of the aperture decreases towards one side, preferably the side opposite a direction from which the respective acoustic valves 13a closes the aperture. For example, the tapered shape comprises a triangular shape, as shown, or a trapezoid shape, exponential shape, or any shape wherein the cross-section transverse to the direction of closing gets narrower towards the end in which the acoustic valves closes the aperture. It will be appreciated that the tapered shape may improve control over the cross-section area, especially over small changes of the area near the position where the valve is almost closed. Alternatively, or in addition to shaping the aperture, also the valve may be shaped to provide similar effect. Also other embodiments may be envisaged to provide a non-linear change of cross-section in response to a linear control of moving elements. For example, instead of rolling, the closing may also slide over the non-linear, e.g. tapered opening. Instead of linearly moving closing means, they may also rotate. For example, one ore more rotating disc may rotate with a constant radial velocity while closing off a non-linearly varying opening.

It will be appreciated that the constructional features as described herein may provide specific benefit in digital control e.g. where a discrete number of control signals and corresponding attenuation steps may be available. But the constructional features as described herein may also provide advantages in analog control e.g. wherein the precision of the control may be improved especially at high attenuations (where the aperture is almost closed). Also it may still better conform even to continuous changes in attenuation as perceived in natural hearing. So in some embodiments, the acoustic filter may be adapted to provide the selection of the attenuation from a continuous sequence of predetermined attenuations based on a selection of the control signal from a corresponding continuous sequence of predetermined control signals. Similarly, each attenuation in the continuous sequence may correspond to the one or more acoustic valves providing the one or more apertures with a respective predetermined acoustic resistance which in some cases may be varied continuously e.g. by an analog signal. The acoustic resistances of subsequent attenuations in the continuous sequence (with arbitrarily small but fixed step size) can be adapted to correspond with a linear increase or decrease in the attenuation of the sound in decibels. So for example, a valve which is controlled by linearly varying analogue control signals, may vary its cross-section non-linearly in order to linearly increase or decrease the attenuation of the sound in decibels.

Figure 6A:
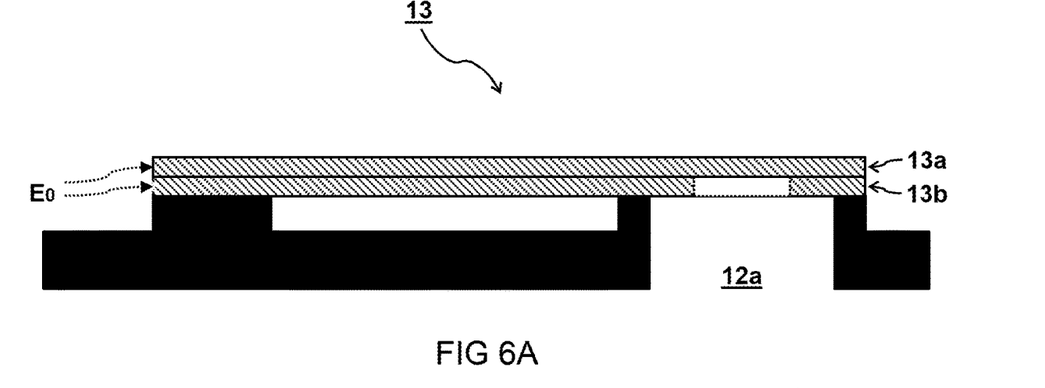
FIGS. 6A-6C schematically illustrate side views of a valve system comprising stacked valves.
Figure 6B:
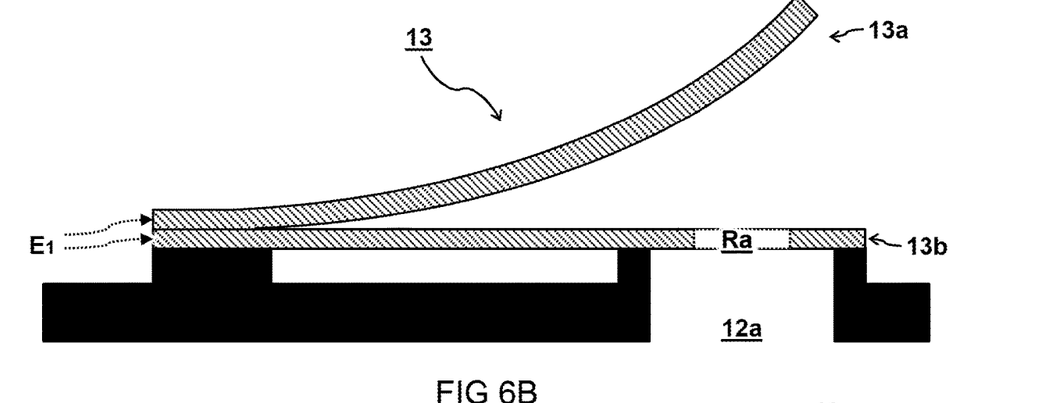
Figure 6C:
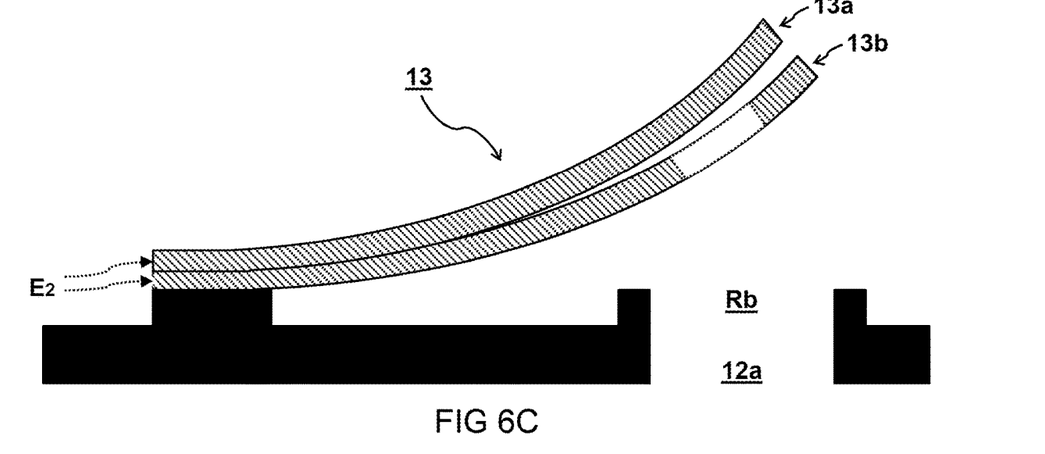

FIGS. 6A-6C schematically illustrate side views of a valve system 13 comprising stacked valves.

In some embodiments, e.g. as shown or otherwise, at least one valve 13b comprises an aperture. In the embodiment shown, the aperture in valve 13b is smaller than an aperture 12a which the valve is configured to cover, e.g. the aperture of the sound passage 12 or an aperture of another valve underneath (not shown). In some embodiments, e.g. as shown, the valve system 13 comprises one or more stacked valves 13a,13b. Preferably, the valves in the stack are individually controllable. In the embodiment shown, a first valve 13a of the stacked valves is configured to at least partially close an aperture in a second valve 13b.

Also more than two valves may be stacked, e.g. three, four, or more (not shown). Preferably, a cross-section area of the one or more apertures in the stacked valves increases from top to bottom towards the respective aperture 12a in the sound passage 12. In this way different effective apertures may be selected depending on which aperture is on top. Alternatively, or in addition to providing the stacked valves with different open areas, the thickness or length of the stacked apertures may already provide a different acoustic resistance.

Figure 7A:
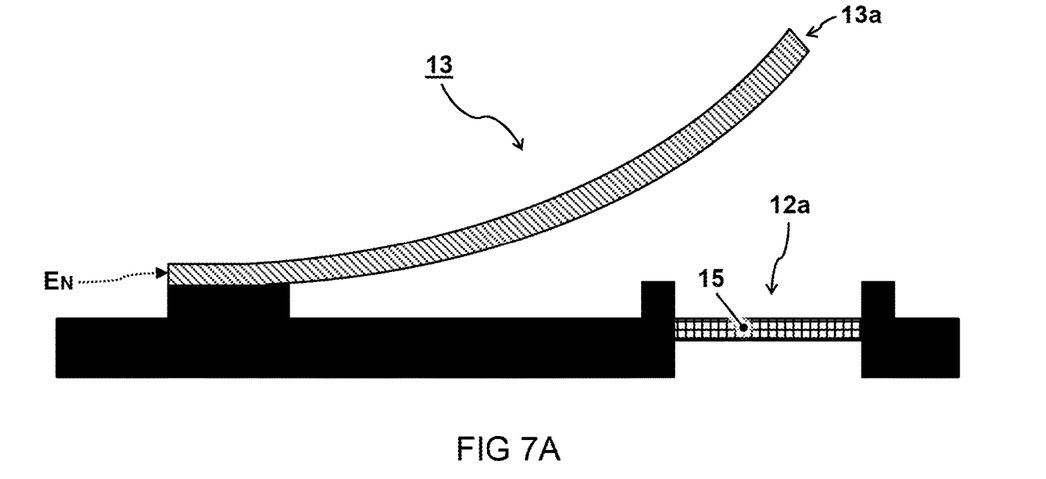
FIGS. 7A-7C schematically illustrate side views of apertures including an acoustic element.
Figure 7B:
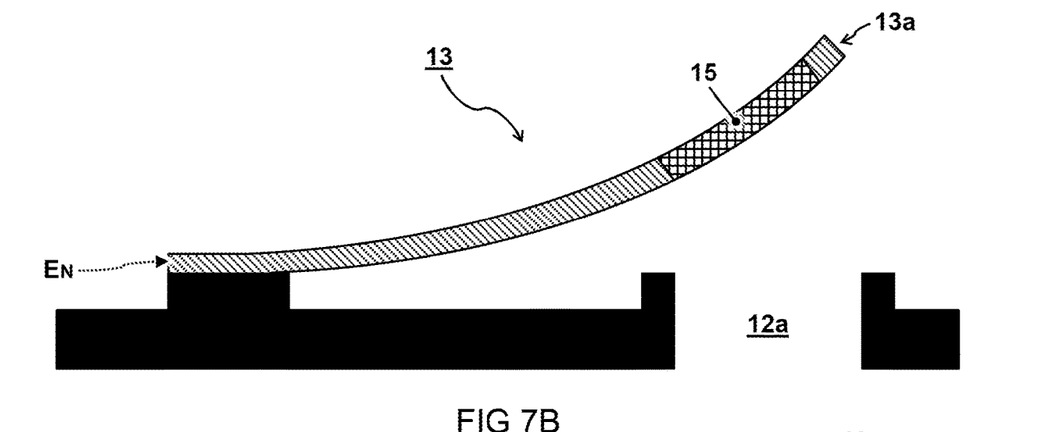
Figure 7C:
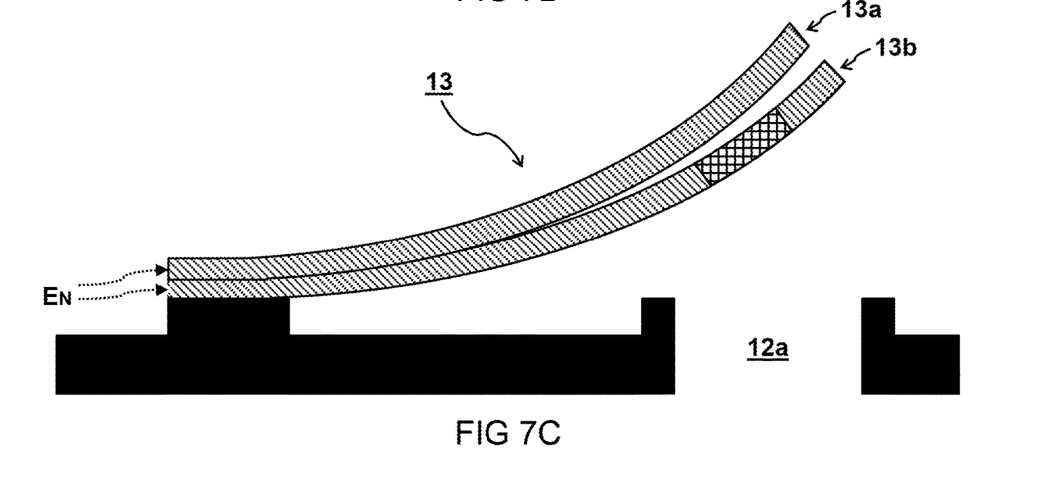

FIGS. 7A-7C schematically illustrate side views of apertures including an acoustic element 15. In some embodiments, one or more of the apertures 12a comprise an acoustic element 15 such as a mesh, flexible membrane, et cetera. For example, a woven or injection molded mesh can be used. In some embodiments, the acoustic element 15 is configured to shape a desired acoustic response e.g. across different frequencies, for one or more of the predetermined attenuations $\Delta S_N$. For example, a membrane may provide a better sound experience from an acoustic generator and a more flat sound transfer from ambient sound into the auditory canal. The acoustic element 15 may alternatively, or additionally be integrated in an aperture of the acoustic valve 13a as shown in FIG. 7B, and/or in a stack of valves as shown in FIG. 7C. Alternatively to being placed in an aperture with a valve, the acoustic element 15 may also be placed in series with one or more valves and/or in a parallel channel (not shown).

For the purpose of clarity and a concise description, features are described herein as part of the same or separate embodiments, however, it will be appreciated that the scope of the invention may include embodiments having combinations of all or some of the features described. Of course, it is to be appreciated that any one of the above embodiments or processes may be combined with one or more other embodiments or processes to provide even further improvements in finding and matching designs and advantages. It is appreciated that this disclosure offers particular advantages to attenuation of ambient sound, and in general can be applied for any application wherein sound is filtered between two places.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context.

The invention claimed is:

1. An acoustic filter comprising
a filter housing placeable or integrated in an earplug to form an acoustical seal between an auditory canal of an ear and an external surroundings;
a sound passage extending through the filter housing for receiving sound from the external surroundings and transmitting the sound into the auditory canal, the sound passage having one or more apertures providing an acoustic resistance for the sound received and transmitted through the sound passage; and
a valve system comprising one or more acoustic valves arranged in the sound passage for controlling the acoustic resistance of the one or more apertures based on a control signal from a controller for selecting an attenuation of a sound pressure level of the transmitted sound compared to that of the received sound;
wherein the acoustic filter is adapted to provide the selection of the attenuation from a sequence comprising a discrete number of three or more predetermined attenuations based on a selection of the control signal from a corresponding sequence of predetermined control signals, wherein each attenuation in the sequence corresponds to the one or more acoustic valves providing the one or more apertures with a respective predetermined acoustic resistance, wherein the acoustic resistances of subsequent attenuations in the sequence are adapted to correspond with a linear increase or decrease in the attenuation of the sound in decibels.

2. The acoustic filter according to claim 1, wherein the sound passage comprises a plurality of apertures, wherein the valve system is configured to provide the predetermined attenuations by combining respective acoustic resistances of the plurality of apertures.

3. The acoustic filter according to claim 2, wherein combinations of sub-states of multiple valves, controlling combinations of different individual acoustic resistances are adapted to provide the predetermined attenuations.

4. The acoustic filter according to claim 3, wherein said number of predetermined attenuations provided by the combination of valves is greater than the number of valves itself.

5. The acoustic filter according to claim 4, wherein at least some of the apertures individually have a different predetermined respective acoustic resistance, wherein the respective acoustic valves are configured to selectively switch between at least two predetermined sub-states changing the respective apertures to provide one of a predetermined selection of acoustic resistances.

6. The acoustic filter according to claim 1, wherein one or more valves are adapted to provide more than two sub-states, including an intermediate state wherein the respective aperture is partially closed off between a fully open state and a fully closed state to provide an intermediate acoustic resistance higher than the fully open state and lower than the fully closed state.

7. The acoustic filter according to claim 1, wherein the sequence of predetermined control signals causes a total cross-section of at least one aperture to sub-linearly decreases between a maximally opened state and a maximally closed state.

8. The acoustic filter according to claim 1, wherein at least one aperture and/or acoustic valve is adapted to provide a non-linear change of its acoustic resistance in response to a linear change of a voltage or current of the control signal.

9. The acoustic filter according to claim 1, wherein at least one aperture and/or acoustic valve is adapted to provide an exponentially changing open area for a linear motion of the acoustic valve with respect to the aperture.

10. The acoustic filter according to claim 1, wherein the valve system comprises one or more stacked valves, wherein the valves in the stack are individually controllable, wherein a first valve of the stacked valves is configured to at least partially close an aperture in a second valve.

11. The acoustic filter according to claim 1, wherein one or more of the apertures comprise an acoustic element such as a mesh or flexible membrane.

12. The acoustic filter according to claim 1, comprising a controller configured and/or programmed to provide a predetermined sequence of volume settings wherein an increase or decrease of the volume setting results in a fixed change of the attenuation in decibels and/or logarithmic change of the transmitted sound pressure level.

13. The acoustic filter according to claim 1 forming part of an earplug.

14. The acoustic filter according to claim 13, further comprising an acoustic generator between the valve and the auditory canal arranged for generating an acoustic signal into the auditory canal.

15. A method for manufacturing an acoustic filter,
the acoustic filter comprising a filter housing placeable or integrated in an earplug to form an acoustical seal between an auditory canal of an ear and an external surroundings; a sound passage extending through the filter housing for receiving sound from the external surroundings and transmitting the sound into the auditory canal, the sound passage having one or more apertures providing an acoustic resistance for the sound received and transmitted through the sound passage; and a valve system comprising one or more acoustic valves arranged in the sound passage for controlling the acoustic resistance of the one or more apertures based on a control signal from a controller for selecting an attenuation of a sound pressure level of the transmitted sound compared to that of the received sound; wherein the acoustic filter is adapted to provide the selection of the attenuation from a sequence comprising a discrete number of three or more predetermined attenuations based on a selection of the control signal from a corresponding sequence of predetermined control signals, wherein each attenuation in the sequence corresponds to the one or more acoustic valves providing the one or more apertures with a respective predetermined acoustic resistance, wherein the acoustic resistances of subsequent attenuations in the sequence are adapted to correspond with a linear increase or decrease in the attenuation of the sound in decibels;

the method comprising:
designing the acoustic filter to provide the discrete number of attenuations which linearly increase or decrease the transmitted sound in decibels; and
storing the corresponding sequence of control signals for control of the acoustic filter.

16. Use of an acoustic filter for controlling attenuation of an external surroundings into an auditory canal, the acoustic filter comprising a filter housing placeable or integrated in an earplug to form an acoustical seal between an auditory canal of an ear and an external surroundings; a sound passage extending through the filter housing for receiving sound from the external surroundings and transmitting the sound into the auditory canal, the sound passage having one or more apertures providing an acoustic resistance for the sound received and transmitted through the sound passage; and a valve system comprising one or more acoustic valves arranged in the sound passage for controlling the acoustic resistance of the one or more apertures based on a control signal from a controller for selecting an attenuation of a sound pressure level of the transmitted sound compared to that of the received sound; wherein the acoustic filter is adapted to provide the selection of the attenuation from a sequence comprising a discrete number of three or more predetermined attenuations based on a selection of the control signal from a corresponding sequence of predetermined control signals, wherein each attenuation in the sequence corresponds to the one or more acoustic valves providing the one or more apertures with a respective predetermined acoustic resistance, wherein the acoustic resistances of subsequent attenuations in the sequence are adapted to correspond with a linear increase or decrease in the attenuation of the sound in decibels;

the use comprising changing the attenuation in discrete steps, wherein in each step a subsequent attenuation in the sequence of predetermined attenuations is selected to linearly increase or decrease the attenuation of the sound in decibels.

* * * * *